United States Patent [19]

Hsiang-Lai et al.

[11] 3,946,745
[45] Mar. 30, 1976

[54] APPARATUS FOR GENERATING POSITIVE AND NEGATIVE ELECTRIC PULSES FOR APPLICATION TO A LIVING BODY FOR THERAPEUTIC PURPOSES

[75] Inventors: Wen Hsiang-Lai; Gaylord Chan, both of Hong Kong, China

[73] Assignee: Biopulse Company Limited, Hong Kong, China

[22] Filed: Mar. 18, 1974

[21] Appl. No.: 452,125

[30] Foreign Application Priority Data
Mar. 22, 1973  United Kingdom............... 13894/73

[52] U.S. Cl............ 128/421; 128/2.1 C; 128/329 A; 128/422
[51] Int. Cl.².......................................... A61N 1/36
[58] Field of Search........... 128/2.1 C, 2.1 R, 172.1, 128/419 C, 419 E, 419 P, 419 D, 419 R, 421, 422, 423, 303.18, 329 A

[56] References Cited
UNITED STATES PATENTS

| | | | |
|---|---|---|---|
| 2,375,575 | 5/1945 | Morland et al. | 128/421 |
| 2,771,554 | 11/1956 | Gratzl | 128/421 |
| 3,563,247 | 2/1971 | Bowers | 128/422 |
| 3,727,616 | 4/1973 | Lenzkes | 128/422 |

*Primary Examiner*—William E. Kamm
*Attorney, Agent, or Firm*—Prutzman, Hayes, Kalb & Chilton

[57] ABSTRACT

Apparatus for treating organisms for therapeutic purposes consists in applying thereto by means of electrodes an electrical signal comprising successive pairs of pulses, the pulses of each pair being of opposite polarity. The apparatus has an electrode arrangement for application to the organism and a signal generator for supplying to the electrode arrangement the signal comprising successive pairs of pulses, the pulses of each pair being of opposite polarity. The generator has controls for varying independently of one another the amplitude of the pulses of each polarity, the duration of the pulses of each polarity, the interval between the pulses of each pair, and the interval between successive pairs of pulses.

2 Claims, 11 Drawing Figures

APPARATUS FOR GENERATING POSITIVE AND NEGATIVE ELECTRIC PULSES FOR APPLICATION TO A LIVING BODY FOR THERAPEUTIC PURPOSES

The present invention concerns apparatus for the application of electrical signals to an organism.

In accordance with the invention there is provided apparatus for treating organisms by applying thereto by means of electrodes an electrical signal comprising successive pairs of pulses, the pulses of each pair being of opposite polarity.

It has been found that the application of signals as defined in the preceding paragraph to a patient has important therapeutic value in certain types of illness. In this connection, it has been observed that the application of pairs of pulses in which the pulses are of opposite polarities is of vital importance in the therapeutic effect obtained. Each pair of pulses of opposite polarity may thus be considered as a unit, and may for convenience be referred to as a "bio-pulse".

As each bio-pulse consists of two pulses, it will be convenient to refer to these as the fore-pulse and the aft-pulse, the fore-pulse being the first pulse of each pair and the aft-pulse the second pulse of each pair.

Due to the nature of the bio-pulse, it is more meaningful to refer to the "density" and "intensity" of the electrical signals rather than to their frequency and voltage respectively.

The invention also includes apparatus as defined in the preceding paragraph but three of which the following properties of the pulses are independently variable: (a) the amplitude of the pulses of each polarity; (b) the duration of the pulses of each polarity; (c) the interval between the pulses of each pair; and (d) the interval between successive pairs of pulses.

The first pulse in each pair may be of either polarity, and the polarity of the pulses in each pair is advantageously reversible.

The invention also includes apparatus for the application of electrical signals to an organism, comprising an electrode arrangement for application to the organism and a signal generator for supplying to the electrode arrangement a signal comprising successive pairs of pulses, the pulses of each pair being of opposite polarity.

The invention further includes apparatus as defined in the preceding paragraph, in which the generator has controls for varying independently of one another: (a) the amplitude of the pulses of each polarity; (b) the duration of the pulses of each polarity; (c) the interval between the pulses of each pair; and (d) the interval between successive pairs of pulses.

The first pulse in each pair may be of either polarity, and the apparatus may advantageously comprise a control for reversing the polarities of the pulses in each pair.

The invention will now be described in more detail, by way of example only and with reference to the accompanying drawings in which.

Figure 1:
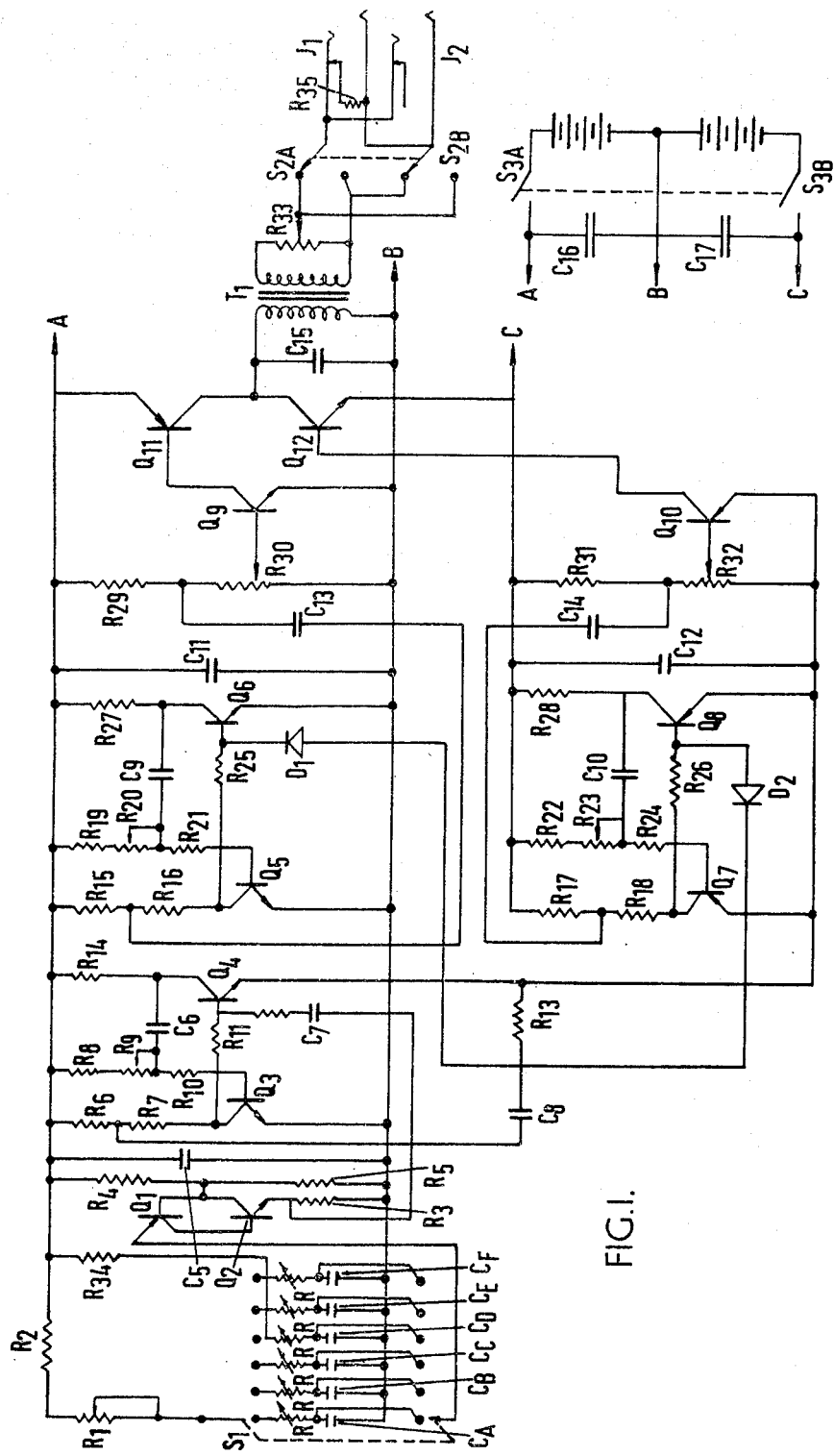
FIG. 1 is a circuit diagram of an electrical signal generator of apparatus for the application of electrical signals to an organism.

Referring to FIG. 1, the generator is powered by eight 1.5 volt batteries divided into two groups so as to give positive and negative 6 volts supplies. Thus a positive voltage of 6 volts is obtained at point A, earth voltage at point B and a negative voltage of 6 volts at point C. Points A and B are joined through a smoothing capacitance C16, and points B and C through a smoothing capacitance C17. Point A is connected to the positive pole of one group of batteries through a switch section $S_3A$ and point C to the negative pole of the other group of batteries through switch section $S_3B$. These two switch sections are ganged together as indicated by the dashed line. Point B is connected directly to the junction of the two groups of batteries.

A variable resistance R1 has one end connected through a resistance R2 to the point A. Its other end is connected to its cursor and to a first cursor of a switch S1. This first cursor is associated with six fixed contacts each of which save one is connected to one end of a pre-set variable resistance R. The other end of each of these resistances is connected to a respective one of a set of capacitance $C_A$ to $C_F$, the other terminals of these capacitances being connected to point B. The junction of each resistances R with its respective capacitance is connected to a fixed terminal associated with a second cursor of the switch S1.

The resistance R connected to capacitance $C_D$ is an exception in that it is connected to point A through a resistance R34 rather than through the switch S1.

The second cursor of switch S1 is connected to the emitter of a PNP transistor Q1 whose collector is connected to the base of a NPN transistor Q2. The base of transistor Q1 is connected to the collector of transistor Q2. The emitter of transistor Q2 is connected to point B through a resistance R3. The base of transistor Q1 is also connected to point A through a resistance R4 and to point B through a resistance R5, the series-connected combination of resistances R4 and R5 being shunted by a capacitance C5.

The collector of a NPN transistor Q3 is connected to point A through the series-connected combination of two resistances R6 and R7. Its emitter is connected to point B. Its base is connected to point A through the series-connected combination of a resistance R8, a variable resistance R9, and a resistance R10. The collector of transistor Q3 is connected to the base of a NPN transistor Q4 through a resistance R11, the base of transistor Q4 being connected to the emitter of transistor Q2 through the series-connected combination of a resistance R12 and a capacitance C7. The junction of variable resistance R9 and resistance R10 is connected to the collector of transistor Q4 through a capacitance C6, this collector being connected to point A through a resistance R14. The emitter of transistor Q4 is connected to the junction of resistance R6 and R7 through the series-connected combination of a resistance R13 and a capacitance C8.

A NPN transistor Q5 has it collector connected to point A through the series-connected combination of resistances R15 and R16. Its emitter is connected to point B, and its base is connected to point A through the series-connected combination of a resistance R19, a variable resistance R20, and a resistance R21. Its collector is connected to the base of an NPN transistor Q6 through a resistance R25, the collector of transistor Q6 being connected to the junction of variable resistance R20 and resistance R21 through a capacitance C9 and through a resistance R27 to point A. The emitter of transistor Q6 is connected to point B. A capacitance C11 connects point A to point B. Point A is also connected to point B through the series-connected combination of a resistance R29 and a variable resistance R30, the cursor of the variable resistance R30 being connected to the base of an NPN transistor Q9. The emitter of transistor Q9 is connected to point B and its collector is connected to the base of a PNP transistor Q11 the emitter of which is connected to point A and the collector of which is connected to that of an NPN transistor Q12. The emitter of transistor Q12 is connected to point C.

The collector of transistor Q12 is connected to point B through a capacitance C15 which is connected in parallel with the primary winding of a transformer T1 whose secondary winding is connected across a variable resistance R33. The cursor of the resistance R33 is connected to a first fixed terminal of each of a pair of ganged change-over switch sections $S_2A$ and $S_2B$. Second fixed contacts of these switch sections are connected together and to one end of the resistance R33. The cursor of each of switch sections $S_2$ is connected to a respective terminal of jack sockets J1 and J2. Socket J1 includes a resistance R35 closing the circuit when no jack plug is connected to the socket.

A PNP transistor Q7 has its collector connected to point C through the series-connected combination of resistances R17 and R18. Its emitter is connected to that of a PNP transistor Q10. Its base is connected to point C through the series-connected combination of a resistance R22, a variable resistance R23 and a resistance R24. The collector of transistor Q7 is connected through a resistance R26 to the base of a transistor Q8, the base of transistor Q8 being connected to the anode of a diode D2 whose cathode is connected to the junction of capacitance C8 and resistance R13 and to the anode of a diode D1 whose cathode is connected to the base of transistor Q6. The emitter of transistor Q8 is also connected to that of transistor Q10, which is also connected to that of Q4.

The collector of transistor Q8 is connected through a capacitance C10 to the junction of variable resistance R23 with resistance R24, and to point C through a resistance R28. The emitter of transistor Q8 is connected to point C through a capacitance C12 which is in parallel with the series-connected combination of a resistance R31 and a variable resistance R32, resistance R31 being connected at one end to point C. The junction of resistance R31 with variable resistance R32 is connected through a capacitance C14 to the junction of resistances R17 and R18. The cursor of resistance R32 is connected to the base of the transistor Q10 the collector of which is connected to the base of transistor Q12.

Figure 2:
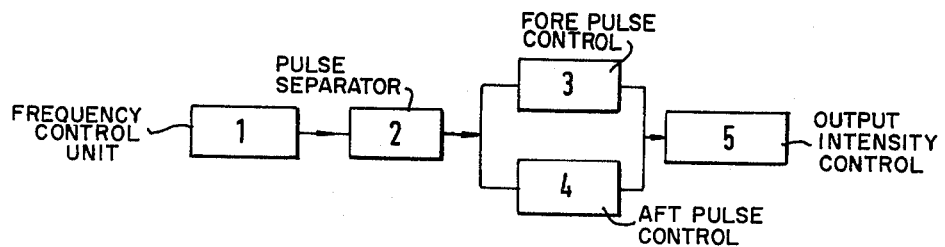
FIG. 2 is a block diagram of the signal generator.

Referring to FIG. 2, this circuit has six basic units, namely the power supply (not shown in FIG. 2), a "density" control unit 1, a fore-pulse and aft-pulse separator 2 a control unit for the fore-pulse 3, a control unit for the aft-pulse 4, and an output unit 5.

The density control unit is basically an oscillator the operational frequency of which can be varied between limits of zero and 2000 Hz by means of a range selector and tuning control. Its output is fed to the fore- and aft-pulse separator.

The separator, when excited by oscillations, generates square waves at a given frequency but with variable pulse width. The leading edge and trailing edge of each square wave are then separately fed to the fore-pulse control unit and the aft-pulse control unit.

These control units are identical except in that they are concerned with opposite polarities. The fore-pulse control unit is also a square wave generator. It produces positive-going pulses with adjustable width. The frequency of these pulses is governed by the fore- and aft-pulse separator.

The aft-pulse control unit produces negative-going pulses.

The fore- and aft-pulses are fed to the output unit, which has two individual input controls which control the input amplitude of the fore- and aft-pulses. Intensity control is provided for adjusting the bio-pulse output. A normal and reverse switch is also provided for reversing the polarities of the two pulses in each bio-pulse.

The operation of each part of the signal generator will now be described with reference to FIGS. 3 to 7.

Figure 3:
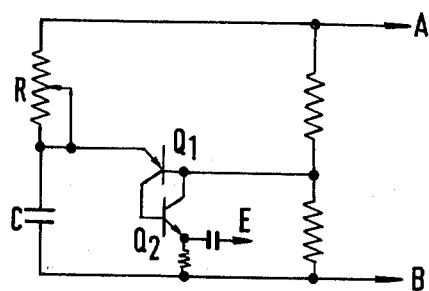
FIGS. 3 to 7 show those parts of the circuit corresponding to the blocks of FIG. 2.

Referring to FIG. 3, the density control unit consists of that part of the circuitry comprising transistors Q1 and Q2. These are connected to form a negative resistance device. Transistors Q1 and Q2 will conduct abruptly when the voltage at the emitter of transistor Q1 is greater than that at its base. Due to the negative resistance effect, capacitance C (i.e. the selected one of the set $C_A$ to $C_F$), will be instantly discharged.

When the base voltage of transistor Q1 exceeds its emitter voltage, this condition is reversed and the capacitance C will be charged through resistance R until the emitter voltage exceeds the base voltage, when the discharging action will be repeated. The repetition rate is controlled by the time constant RC.

The RC combinations are chosen and can be selected by means of the range switch S1 to give oscillations in the following ranges:

Position 1: 0 to 2Hz
Position 2: 2 to 8.3 Hz
Position 3: 8.3 to 50 Hz
Position 4: 125 Hz
Position 5: 50 to 333Hz
Position 6: 333 to 2000 Hz.

Figure 4:
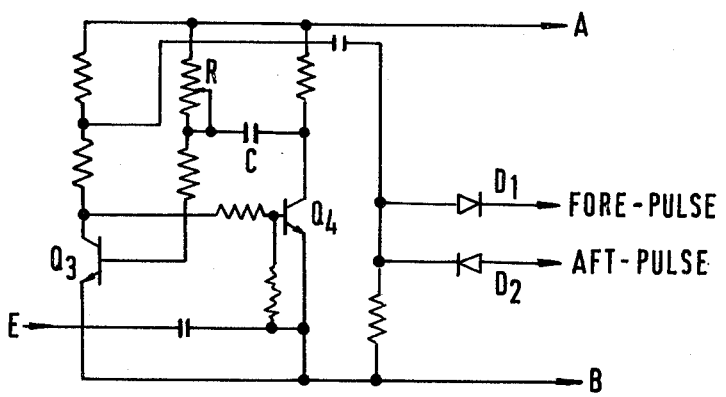

The output at E is applied to the fore- and aft-pulse splitter shown in FIG. 4.

Referring to FIG. 4, the fore- and aft-pulse separator consists of that part of the circuit comprising transistors Q3 and Q4. These form a one-shot multivibrator. When a trigger pulse is applied to transistor Q4 it will conduct for a period determined by the time constant RC in its collector circuit.

The square wave pulse is picked up from the collector circuit of transistor Q3. Its leading and trailing edges are separated by diodes D1 and D2. The separated positive-going and negative-going pulses are fed to the respective control units. A separation of the fore- and aft-pulses of up to 1.4 milliseconds is available.

Figure 5:
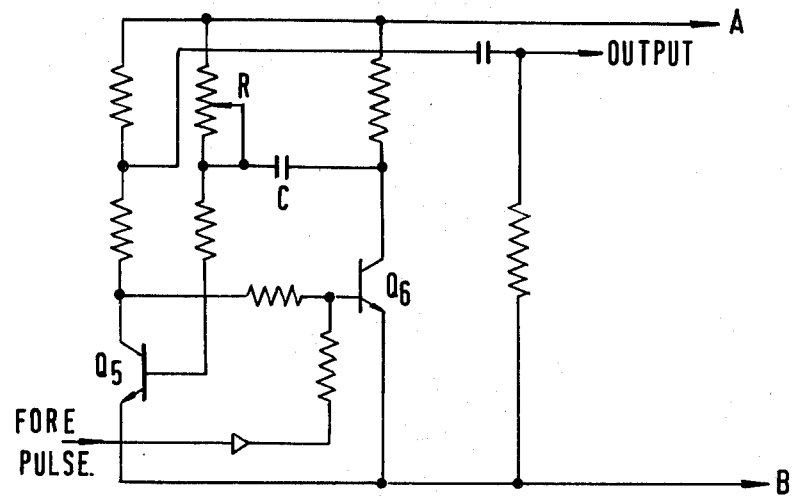

Referring to FIG. 5, the fore-pulse control unit consists of that part of the circuit comprising transistors Q5 and Q6. These transistors also form a one-shot multivibrator. When transistor Q6 is triggered it conducts for a period determined by the time constant RC in its collector circuit. It has a maximum span of 1.4 milliseconds. The positive-going square wave pulse is picked up from the collector circuit of transistor Q5 and is fed to the following circuit stage.

Figure 6:
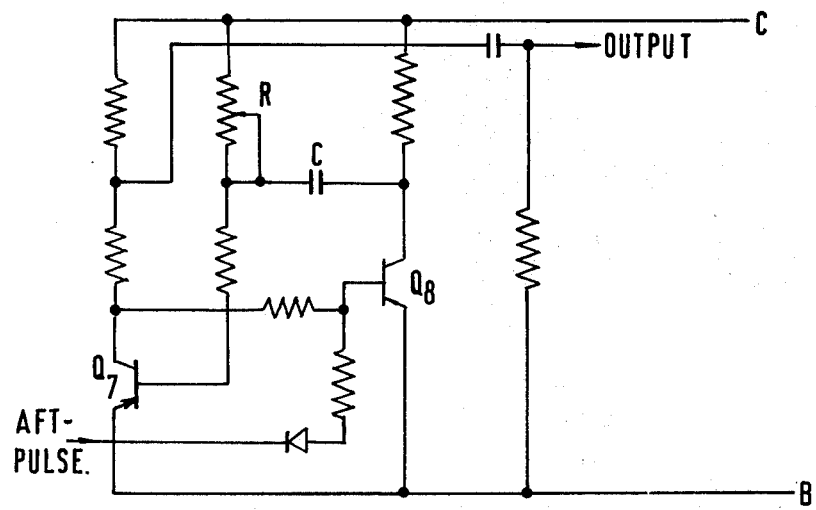

Referring to FIG. 6, the aft-pulse control unit is that part of a circuit comprising transistors Q7 and Q8. This unit is identical to the fore-pulse control unit except that it deals with the opposite polarity, so that PNP transistors are used rather than NPN transistors. The negative-going pulse is picked up from the collector circuit of transistor Q7 and has a maximum width of 1.4 milliseconds.

Figure 7:
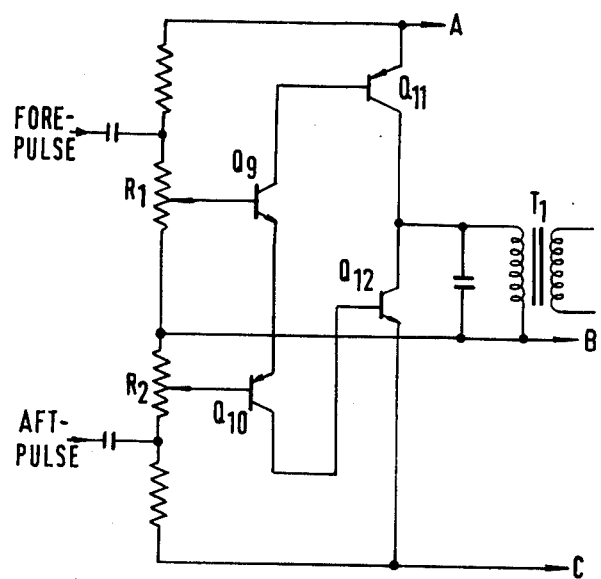

Referring to FIG. 7, the output unit consists of that part of the circuit comprising transistors Q9 to 12. The output unit consists of a positive pulse amplifier comprising transistors Q9 and Q11 and a negative pulse amplifier comprising transistors Q10 and Q12. Transistors Q9 and Q10 are a matched pair, as are transistors Q11 and Q12.

Each amplifier has an input control, resistance R1 and R2 respectively. The bio-pulse output is coupled to the load, i.e. the electrode arrangement, through the transformer T1. The resistance R35 is a 1 kilohm dummy load connected to the output jack socket to facilitate signal checking.

The signal generator is thus provided with controls for varying independently of one another: (a) the amplitude of the pulses of each polarity (R30, R32); (b) the duration of the pulses of each polarity (R20, R23); (c) the interval between the pulses of each group (R9); and (d) the interval between successive groups (R). The circuit also includes a control for reversing the polarities of the pulses in each group (S$_2$A, S$_2$B).

The circuit is shown to include two output jacks J1 and J2. One of these may be used for monitoring the bio-pulse signal by means of an oscilloscope, or as an additional output.

Each electrode arrangement may consist of a pair of electrodes connected to a jack plug, and various forms of electrode may be used. For example, each may consist of a metal "crocodile" clip which may be attached to an acupuncture needle.

Alternatively, each electrode may consist of a spring-loaded ear-ring. As another alternative, each electrode may consist of a metal disc.

Figure 8:
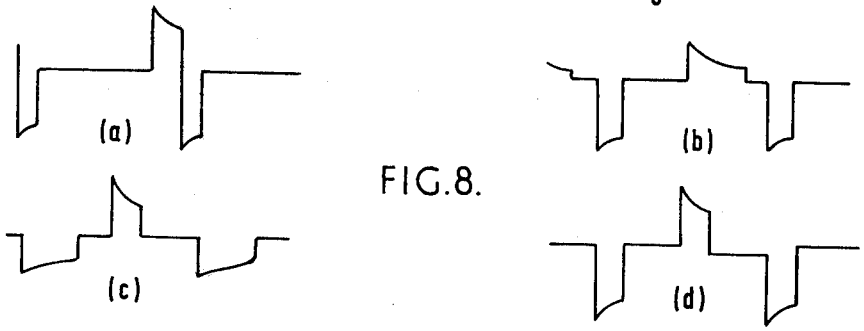
FIG. 8 shows some output signals provided by the generator.

FIG. 8 shows the output signal of the generator with various pulse amplitudes and separations.

The apparatus as so far described is a multi-purpose unit, suitable for use in a wide variety of therapeutic applications. For many applications a restricted range of control will suffice, or even none at all.

For example, experience may indicate that many asthma sufferers obtain significant relief from a unit having certain bio-pulse parameters. Units can then be produced in large or small quantities exclusively for asthma sufferers. The elimination of the unnecessary control functions simplifies the apparatus and so reduces its cost.

Figure 9:
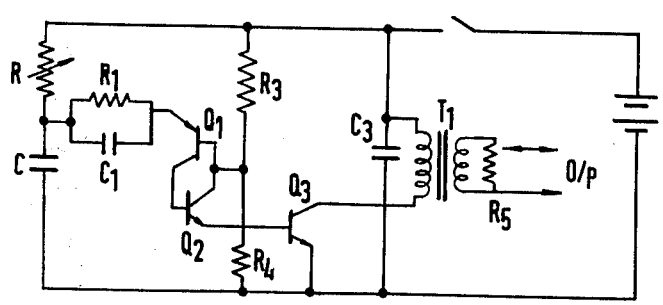
FIG. 9 shows a simplified apparatus.

FIG. 9 shows simplified apparatus, the part of which to the left of and including resistances R3 and R4 being identical to the density control unit shown in FIG. 3 except for the network R1 C1 connected between the emitter of transistor Q1 and the junction of resistance R and capacitance C. This network is a pulse width control circuit, value of R1 being so selected as to produce a required pulse width by controlling the discharge time of capacitance C through transistors Q1 and Q2.

The emitter of transistor Q2 is connected to an output unit comprising an NPN transistor Q3 having its base connected to the emitter of transistor Q2, its emitter connected to the negative pole of a supply provided by two 1.5 volt dry cells, and its collector connected to the positive supply pole through the primary winding of a transformer T1. The secondary winding is shunted by a variable resistance R5 across which the output pulses appear.

Figure 10:
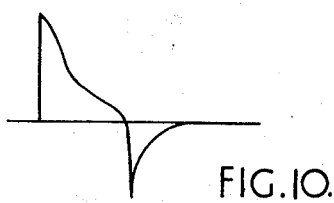
FIGS. 10 and 11 show output waveform of the apparatus.

The density control unit produces a square wave signal which is faithfully amplified by transistor Q3. Due to the back e.m.f. of the transformer T1, however, the output from the transformer distorts each pulse and has at the end of each pulse a spike of the opposite polarity. This particular circuit produces positive-going pulses followed by negative going spikes. As clearly seen in FIG. 10, the transformer output thus constitutes a "bio-pulse", the parameters of which are determined by the fixed component values and the settings of R and R5.

A further modification (not shown in the drawings) which may be made to both the multi-purpose unit of FIG. 1 and the simplified unit of FIG. 9 is to replace the output transformer T1 by a pair of resistances connected in parallel.

Figure 11:
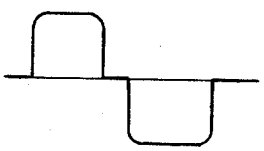

This has the advantage of producing an undistorted output, as shown in FIG. 11, and also reduces the cost of the unit. A disadvantage, however, is that the patient is no longer isolated from the direct current source. This is why two resistances in parallel are used instead of a single resistance. Were a single resistance to be used and to go open circuit, the output power from the unit would be drained through the patient. Using two resistances, however, open-circuiting of one of them will result in the output current flowing through the other, rather than through the patient. The chances that the two resistances will both become open-circuited after very small.

Beneficial results have been obtained in using the bio-pulse in connection with drug addiction, asthma, insomnia and facial palsy. The bio-pulse is also useful for the relief of pain and has anaesthetic properties.

We claim:

1. Apparatus for generating positive and negative electrical pulses for application to a living body for therapeutic purposes comprising pulse generating means for producing at the output terminals thereof a succession of pairs of electrical pulses of opposite polarity and with adjustable repetition rate, pulse separating means for adjusting the time interval between pulses of opposite polarity of each pair of pulses and for supplying positive pulses to a first output terminal and negative pulses to a second output terminal, first pulse forming means connected to the first output terminal for adjusting the amplitude and width of the positive pulses, second pulse forming means connected to the second output terminal for adjusting the amplitude and width of the negative pulses, and output means for combining the pulses from the first and second pulse forming circuit into an output signal of the apparatus.

2. The apparatus of claim 1 wherein said pulse separating means includes means for adjusting the time of occurrence of pulses of opposite polarity with respect to each other independently of any other adjustment.

* * * * *